US008562610B2

(12) United States Patent
Chabansky et al.

(10) Patent No.: US 8,562,610 B2
(45) Date of Patent: Oct. 22, 2013

(54) COMPLIANT DEVICE AND METHOD FOR CUTTING AN INTERVERTEBRAL DISC

(75) Inventors: Bruce Chabansky, Palo Alto, CA (US); Calin Druma, Cupertino, CA (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 514 days.

(21) Appl. No.: 12/835,357

(22) Filed: Jul. 13, 2010

(65) Prior Publication Data

US 2012/0016367 A1 Jan. 19, 2012

(51) Int. Cl.
*A61B 17/16* (2006.01)

(52) U.S. Cl.
USPC .......................................................... 606/79

(58) Field of Classification Search
USPC ............ 606/79–85, 86 R, 167–171, 176–179
See application file for complete search history.

(56) References Cited

U.S. PATENT DOCUMENTS

| 5,285,795 | A | 2/1994 | Ryan et al. |
| 5,472,426 | A | 12/1995 | Bonati et al. |
| 5,749,828 | A * | 5/1998 | Solomon et al. ............... 600/141 |
| 5,785,647 | A | 7/1998 | Tompkins et al. |
| 7,585,300 | B2 * | 9/2009 | Cha .................................. 606/80 |
| 7,647,123 | B2 | 1/2010 | Sharkey et al. |
| 7,682,378 | B2 | 3/2010 | Truckai et al. |
| 7,708,749 | B2 | 5/2010 | Simpson et al. |
| 2010/0262147 | A1 * | 10/2010 | Siegal et al. ..................... 606/80 |

* cited by examiner

*Primary Examiner* — Kevin T Truong
*Assistant Examiner* — Christopher Beccia (57) ABSTRACT

Devices for cutting an intervertebral disc that may include an elongated shape with a distal end and a proximal end and being sized for insertion into an intervertebral space. The devices may include a number of articulating segments that are movably connected together to be shaped in a variety of angular orientations to conform to the shape of the intervertebral disc. The segments may include one or more exposed cutting surfaces that cut the disc as the device is moved through the intervertebral space.

15 Claims, 8 Drawing Sheets

COMPLIANT DEVICE AND METHOD FOR CUTTING AN INTERVERTEBRAL DISC

BACKGROUND

The present application is directed to a device for cutting an intervertebral disc and, more particularly, to a device constructed from a number of segments that are connected together in an articulating manner to adjust an angular orientation.

The spine is divided into a variety of regions including the cervical, thoracic, and lumbar regions. The cervical region includes the top seven vertebral members identified as C1-C7. The thoracic region includes the next twelve vertebral members identified as T1-T12. The lumbar region includes five vertebral members L1-L5. The vertebral members of the spine are aligned in a curved configuration that includes a cervical curve, thoracic curve, and lumbosacral curve. Intervertebral discs are positioned between the vertebral members and permit flexion, tab, lateral bending, and rotation.

Various conditions may lead to damage of the intervertebral discs and the vertebral members. The damage may result from a variety of causes including a specific event such as trauma, a degenerative condition, a tumor, or infection. Damage to the intervertebral discs and vertebral members can lead to pain, neurological deficit, and/or loss of motion.

Various surgical procedures that remove a portion or entirety of an intervertebral disc are performed to alleviate ailments of the spine. Current surgical devices are constructed to fit within the intervertebral space and cut the intervertebral disc. However, these devices are constructed to remove a limited portion of the intervertebral disc. Many of the devices operate in a linear manner in which they are inserted into the intervertebral space in an insertion direction, and moved back-and-forth manner to only cut linear channels. These devices are not compliant enough to remove disc material close to the cortical walls of the vertebral members.

SUMMARY

The present application is directed to devices and methods for cutting an intervertebral disc. One embodiment may include a number of cylindrical segments each having a first end and an opposing second end positioned a fixed distance apart. The first end may have a pair of outwardly extending protrusions positioned on opposing sides of the segment. The second end may have a pair of receptacles having a shape that matches the pair of protrusions and being on the same opposing sides of the segment. One of the first and second ends may have a sharpened cutting surface. The plurality of segments may be attached in an end-to-end articulating arrangement with the protrusions of a first one of the plurality of segments positioned in the receptacles of an adjacent one of the plurality of segments. The protrusions and the receptacles may be attached together and aligned along a longitudinal axis for the plurality of segments to be movable in a variety of angular positions in a first plane and prevented from moving in a second plane that is perpendicular to the first plane.

The device may include an elongated body having a plurality of segments arranged in an end-to-end orientation. Each of the segments may have a pair of protrusions, a pair of receptacles, a tab, and a slot. A number of articulating joints may be positioned along a length of the body. Each of the joints may be formed by one of the pair of protrusions positioned within one of the pair of receptacles. A number of cutting surfaces may be positioned along the length of the body. A number of connections may be positioned along the length of the body. Each of the connections may be formed by one of the tabs positioned within one of the slots.

The device may include a number of segments attached together in an end-to-end orientation and being pivotable relative to each other. Each of the plurality of segments may include a body with a first end and a second end, a pair of protrusions extending outward beyond the first end and being spaced apart on opposing sides of the segment, a pair of receptacles extending into the second end and being spaced apart on the opposing sides of the second end, a first section on the first end positioned at a first angular orientation relative to a longitudinal axis of the segment, a second section on the first end and spaced apart from the first section and positioned at a different second angular orientation relative to a longitudinal axis of the segment, and a first cutting edge extending along at least one of the first and second sections. A distal member may be attached to a distal one of the plurality of segments. A proximal member may be attached to a proximal one of the plurality of segments.

The various aspects of the various embodiments may be used alone or in any combination, as is desired.

DETAILED DESCRIPTION

The present application is directed to devices and methods for cutting an intervertebral disc. The devices include an elongated shape with a distal end and a proximal end and being sized for insertion into an intervertebral space. The devices include a number of articulating segments that are movably connected together to be shaped in a variety of angular orientations to conform to the shape of the intervertebral disc. The segments include one or more exposed cutting surfaces that cut the disc as the device is moved through the intervertebral space.

Figure 1:
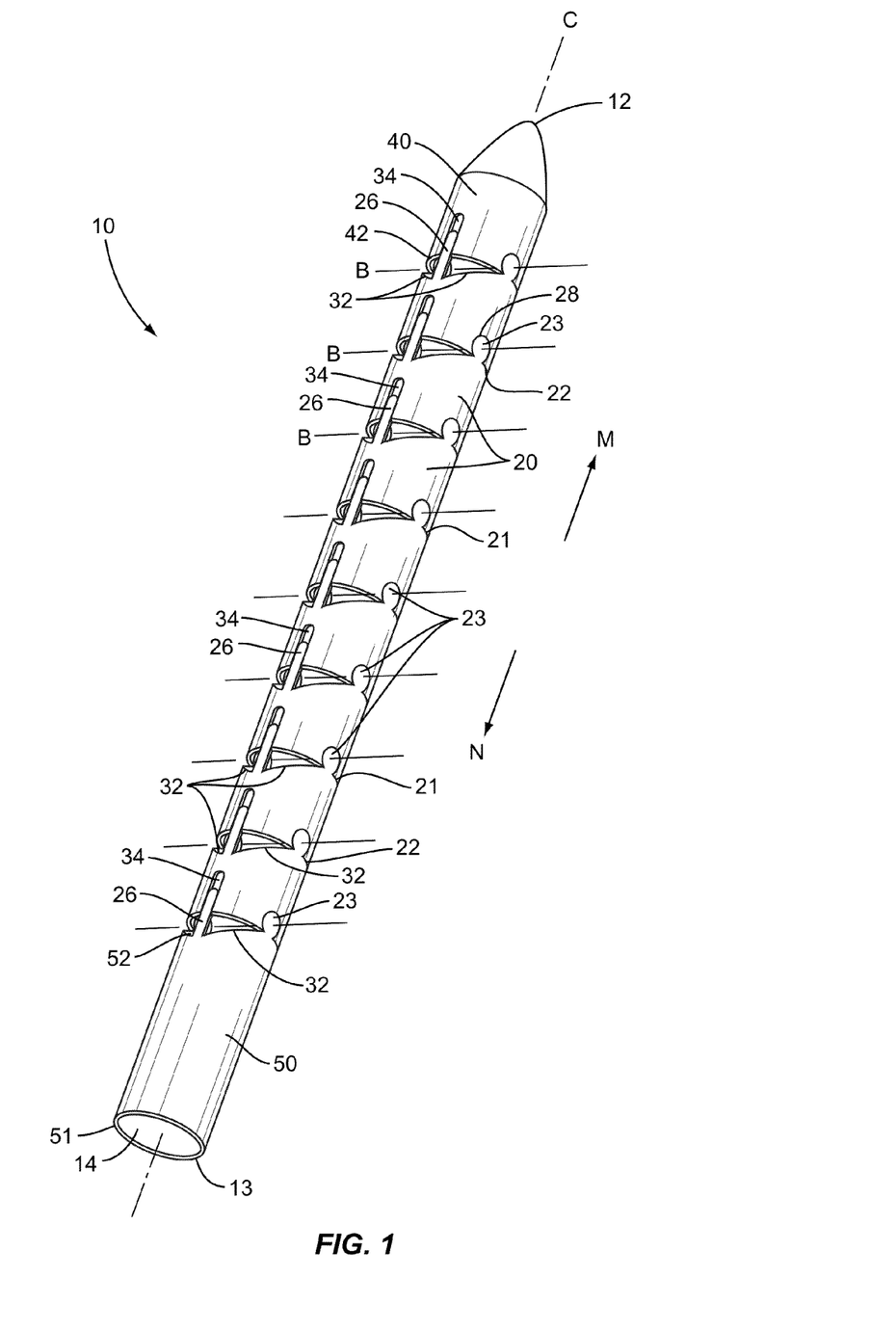
FIG. 1 is a perspective view of cutting device in a straight orientation according to one embodiment.

FIG. 1 illustrates one embodiment of a device 10 for cutting a disc. The device 10 includes an elongated shape with a distal end 12 and a proximal end 13. The device 10 may further include a hollow interior space 14. Two or more articulating segments 20 are attached together and positioned along the length of the device 10. Each pair of articulating segments 20 are movable about a plurality of axes B for adjusting the shape of the device 10. The device 10 may also include a distal member 40 and a proximal member 50.

Pairs of segments 20 are positioned along one or more sections of the device 10. The pairs are connected in an articulating manner to be adjustable about an axis B. This provides for the device 10 to be shaped to conform to the intervertebral space to cut the disc. The segments 20 may each include the same or different shapes and/or sizes. In one embodiment as illustrated in FIG. 1, each of the segments 20 includes the same shape and size.

Figure 2:
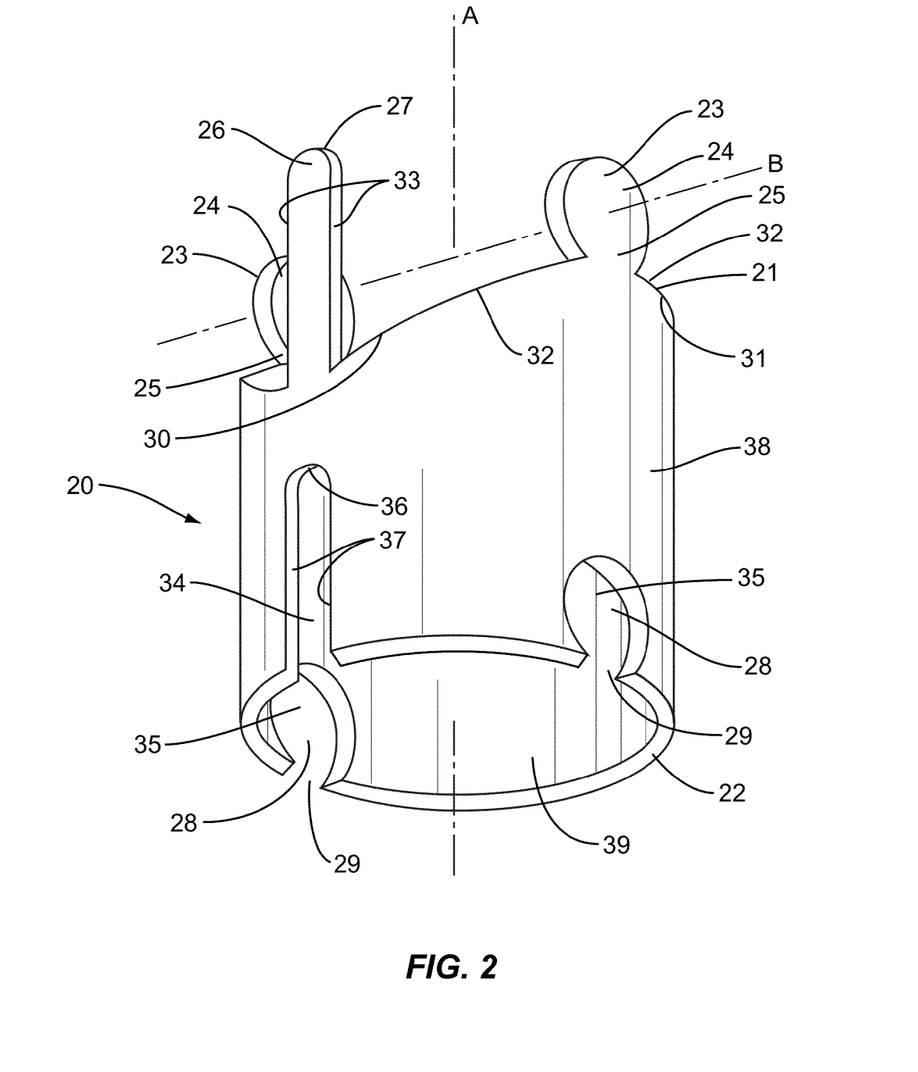
FIG. 2 is a perspective view of a first side of a segment according to one embodiment.
Figure 3:
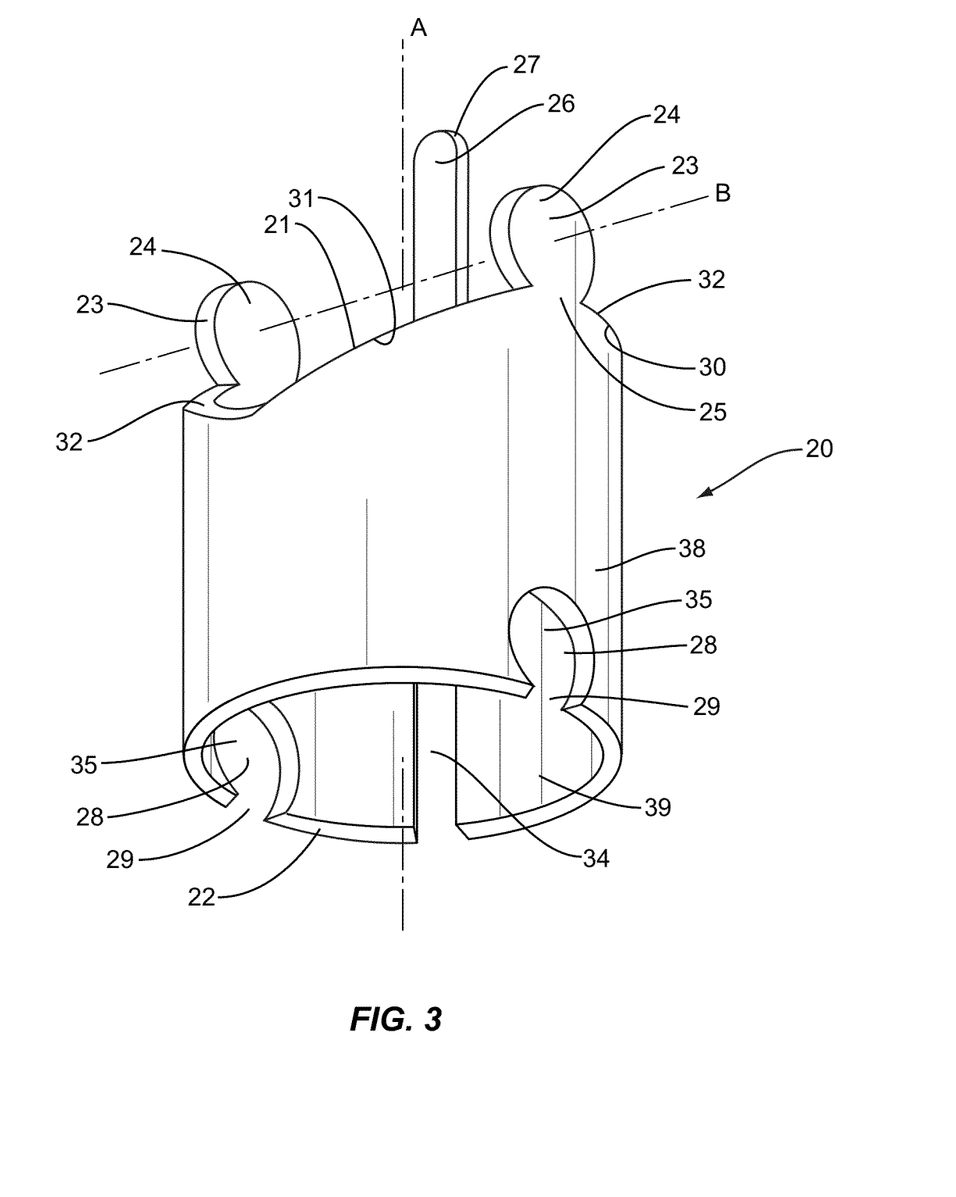
FIG. 3 is a perspective view of a second side of a segment according to one embodiment.

One embodiment of a segment 20 is illustrated in FIGS. 2 and 3. The segment 20 includes a main body 38 with a cylindrical shape having a hollow interior 39, a first end 21, and a second end 22. The body 38 of FIGS. 2 and 3 includes a circular sectional shape, although other embodiments may include different shapes (e.g., oval, polygonal). The body 38 includes a longitudinal axis A that extends through the first and second ends 21, 22. The thickness of the walls of the body 38 may be the same throughout the body 38, or may vary. Another embodiment includes the body 38 being substantially solid with no hollow interior space 39.

A pair of protrusions 23 extends outward beyond the first end 21 of the body 38 and are positioned on diametrically opposed sides of the body 38. Each of the protrusions 23 may include the same shape as illustrated in FIGS. 2 and 3, with other embodiments having a first protrusion 23 with a first shape and a second protrusion 23 with a different second shape. The protrusions 23 include a head 24 and a narrow neck 25. The head 24 includes a greater width than the neck 25. The head 24 includes a rounded shape to facilitate the articulating movement with the adjacent segment 20.

Figure 4:
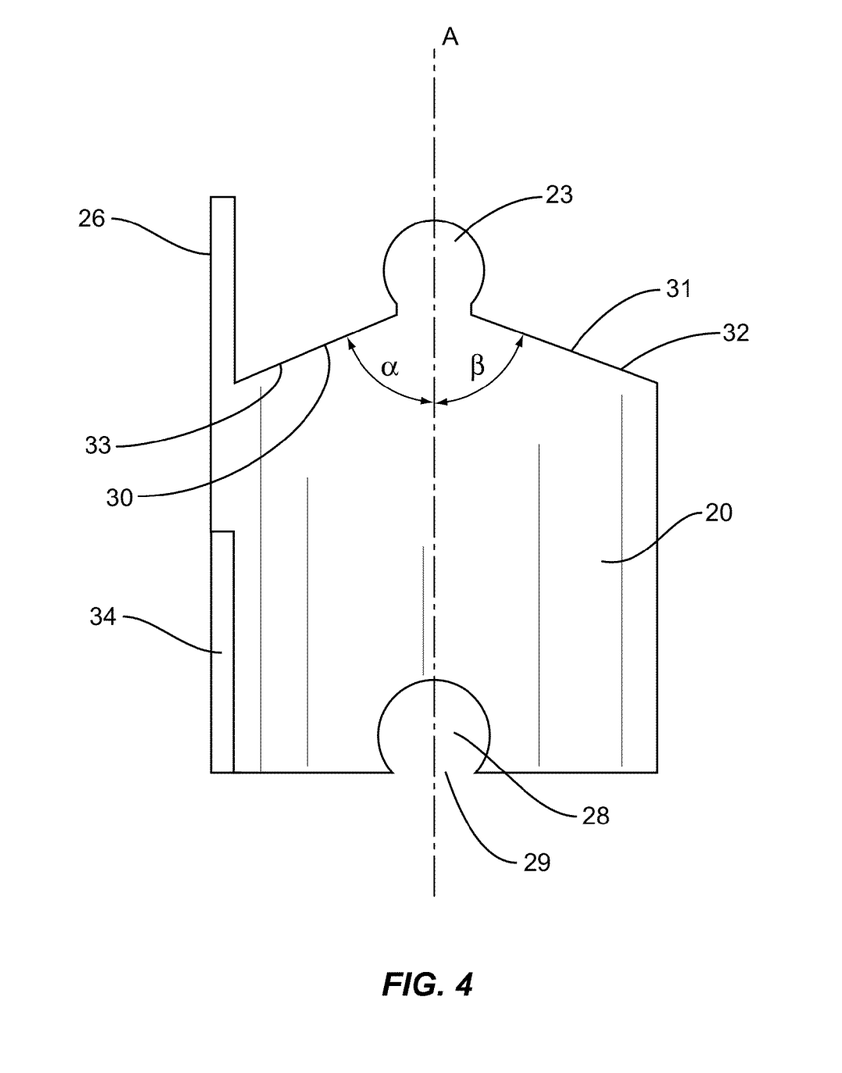
FIG. 4 is a side view of a segment according to one embodiment.

The first end 21 of the body 38 is divided into a first section 30 that extends on a first side of the protrusions 23, and a second section 31 that extends on a second side of the protrusions 23. Portions of the sections 30, 31 may be positioned at various angular orientations relative to the longitudinal axis A. The angles provide pivoting space for the pair of segments 20. As best illustrated in FIG. 4, the first edge 30 forms an angle α relative to the longitudinal axis A, and the second edge 31 forms an angle β. The angles α and β may be the same as illustrated in FIG. 4, or may be different. One embodiment includes angle α being about 90 degrees, and angle β being about 45 degrees.

The body 38 also includes a tab 26 that extends outward from the first end 21. The tab 26 includes an elongated slender shape with a pair of parallel sidewalls 33 that terminate at a tip 27. The tab 26 includes a height measured between the first end 21 and the tip 27. In one embodiment, the tip 27 is positioned inward from a top surface of the protrusions 23 (i.e., the protrusions form the outer-most extent of one side of the segment 20). In one embodiment, the tab 26 is placed 90° to the pivoting axis B and function to allow motion about the axis B and reduce and/or eliminate motion transverse to the axis B as will be explained below.

The second end 22 is positioned opposite from the first end 21. In one embodiment as illustrated in FIGS. 2 and 3, the second end 22 is substantially flat and lies within a plane. Other embodiments may include the second end being non-planar and having one or more angled sections. The second end 22 includes a pair of receptacles 28 shaped and sized to receive the pair of protrusions 23. As with the protrusions 23, the receptacles 28 are positioned on diametrically opposite sides of the body 38. The receptacles 28 are shaped to receive the protrusions 23 and allow for articulating movement about the axis B. FIGS. 2 and 3 include the receptacles 28 having a rounded shape that conforms to the rounded protrusions 23. The receptacles 28 include a narrow inlet 29 that accommodates the neck 25 of the protrusions 23, and an enlarged portion 35 that accommodates the heads 24 of the protrusions 23. For each segment 20, the receptacles 28 may have the same or different shapes.

The protrusions 23 and receptacles 28 are configured to prevent detachment of the segments 20 upon application of an axial force along the longitudinal axis A. The enlarged head 24 is maintained in the enlarged portion 35 of the receptacle 28 thus preventing detachment. Specifically, the reduced width of the inlet 29 prevents the wider head 24 from escaping.

The second end 22 also includes a slot 34 that extends into the body 38 and is sized to receive the tab 26 of an adjacent segment 20. The slot 34 includes a pair of parallel sidewalls 37 and a terminal end 36. A width of the slot 34 measured between the sidewalls 37 is greater than or equal to a width of the tab 26. In one embodiment, a height of the slot 34 measured between the second end 22 and the end 36 is greater than the height of the tab 26.

One or more cutting surfaces 32 are positioned on the body 38 for cutting the disc. The cutting surfaces 32 may include a sharpened edge formed on the exposed surfaces of the ends 21, 22 of the body 38. The cutting surfaces 32 may include a tapered section formed into one or both of the opposing walls of the body 38. The cutting surfaces 32 may be flat or may be serrated.

In one embodiment, the body 38 includes a pair of cutting surfaces 32 on the first end 21. A first cutting surface 32 is positioned along the first section 30, and a second cutting surface 32 is positioned along the second section 31. The first cutting surfaces 32 may extend along the entirety of the sections 30, 31 between the pair of protrusions 23, or may be isolated to one or more limited lengths of the sections 30, 31. Another embodiment features a cutting surface 32 on just one of the sections 30, 31 of the first end 21.

A cutting surface 32 may also be positioned on the second end 22 of the body 38. The cutting surface 32 may extend around the entirety of the second end 22, or along one or more sections of the second end 22.

The segments 20 are attached together in an articulating manner for the device 10 to be movable to various angular positions. As illustrated in FIG. 1, one of the protrusions 23 of each segment 20 are aligned along a first side of the device 10, and the second protrusions are aligned along an opposing second side of the device 10. Likewise, the tabs 26 and corresponding slots 34 are aligned along the length of the device 10.

Figure 5:
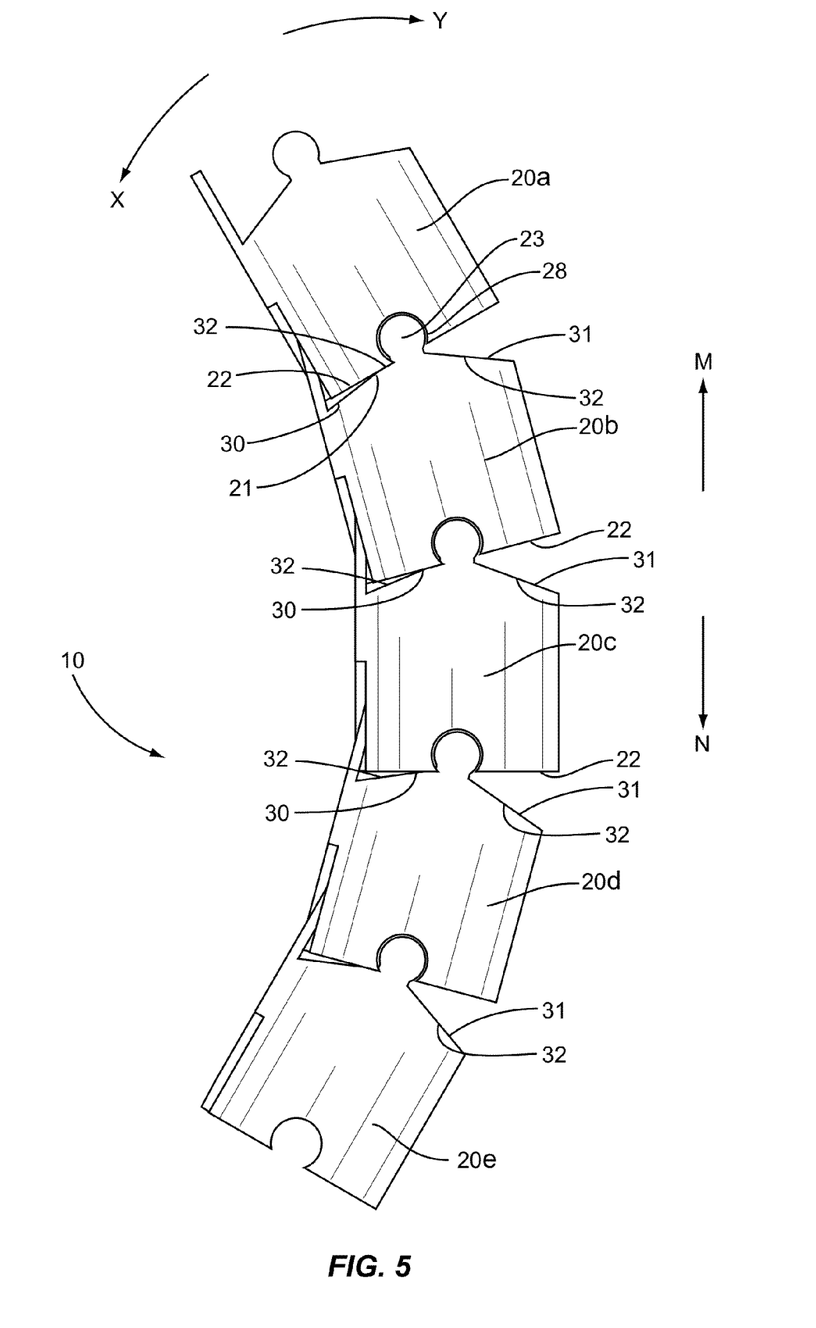
FIG. 5 is a perspective view of cutting device in a curved orientation according to one embodiment.

The extent of articulating movement between the adjacent segments 20 is defined by the shape of the first end 21 of a first segment 20 and the shape of the second end 22 of the adjacent segment 20. As illustrated in FIG. 5, the extent of movement in a first direction of the first segment 20a relative to the second segment 20b is controlled by the second end 22 of the first segment 20a contacting against the first end 21 of the second segment 20b. Specifically, movement in a first direction X (i.e., to the left as illustrated in FIG. 5) is limited by the second end 22 contacting against the first section 30. Movement in the second direction Y (i.e., to the right as illustrated in FIG. 5) is limited by the second end 22 contacting against the second section 31.

Figure 6:
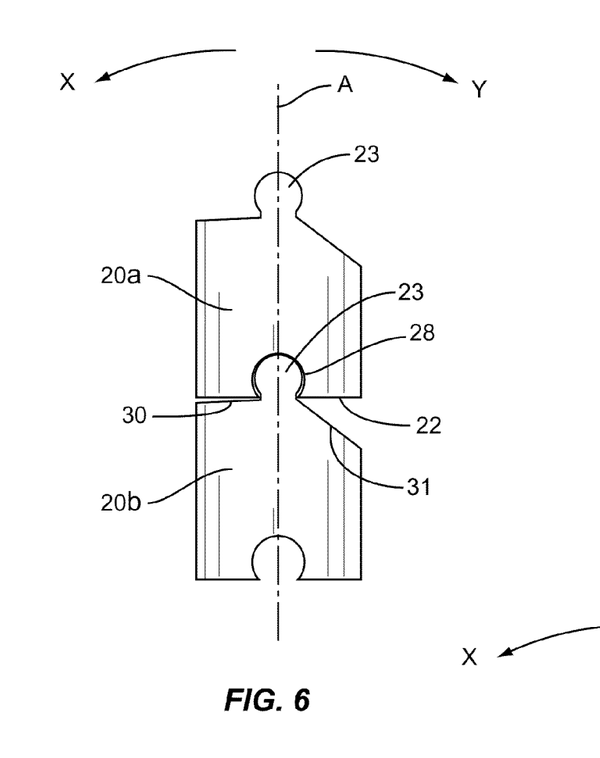
FIG. 6 is a side view of a pair of segments attached together in an articulating manner according to one embodiment.

The movement in the first and second directions is equal with the second end 22 being flat and the first end 21 including angles α, β that are the same for the first and second sections 30, 31. FIG. 5 includes segments 20a-20e with these shapes. Other embodiments may include segments 20 that cause unequal movement in the first and second directions. FIG. 6 includes a first segment 20a with flat second end 22, and a second segment 20b with first and second sections 30, 31 oriented at different angles relative to the longitudinal axis A. The first section 30 is at a larger angle relative to the longitudinal axis A thus restricting the amount of movement in the first direction X. The amount of movement in direction X may be zero, or may be a very small amount. The second section 31 is at a smaller angle relative to the longitudinal axis A thus allowing for a greater extent of movement in the second direction Y.

Figure 7:
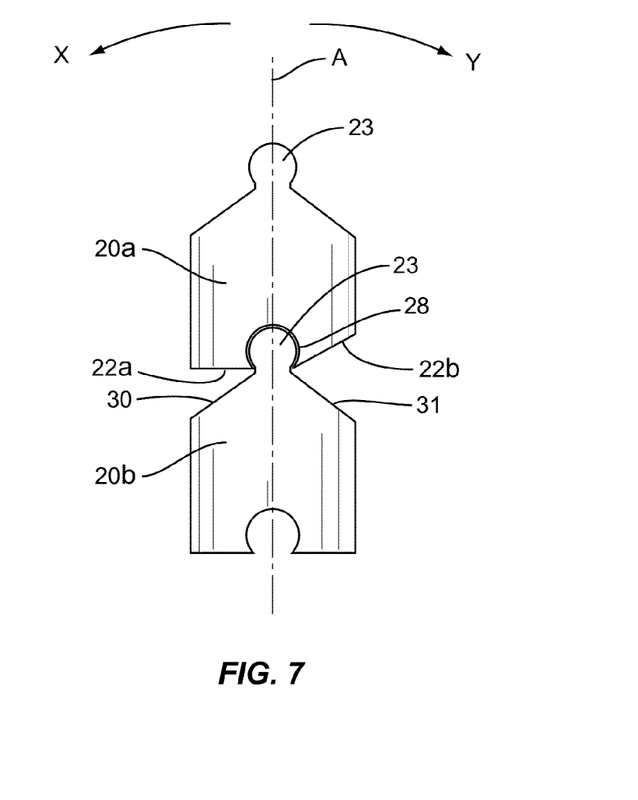
FIG. 7 is a side view of a pair of segments attached together in an articulating manner according to one embodiment.

FIG. 7 includes the first segment 20a having a non-planar second end 22 with sections at different angular orientations. A first section 22a is positioned at a first angular orientation relative to a longitudinal axis A and a second section 22b is at a different second angular orientation. The second segment 20b includes first and second sections 30, 31 at different angular orientations. The orientations of the first sections 22a, 30 provide for a first amount of movement in the first direction X, and the orientations of the second sections 22b, 31 provide for a second amount of movement in the second direction Y.

The device 10 may further include segments 20 with different shapes on the first and second ends 21, 22 attached together along the length. These different shapes may provide for different amounts of angular movement in one or both of the different directions X, Y along different sections of the length. By way of example, the extent of movement in the first direction X between a first pair of adjacent segments 20 may be a first amount, and an extent of movement in the first direction X between a second pair of adjacent segments 20 may be a different second amount.

In one embodiment, the height of the tab 26 is less than the height of the corresponding slot 34. Therefore, the tip 27 of the tab 26 does not contact against the end 36 of the slot 34 and limit the extent of articulating movement. In another embodiment, the tab 26 is longer than the slot 34. The tip 27 of the tab 26 contacts against the end 36 of the slot 34 and limits further movement in that direction.

The attachment of the segments 20 provides for movement within a single plane. This movement provides for positioning the device 10 at the various angular positions within the plane to cut the disc. Using FIG. 5 as an example, the movement in the first direction X and second direction Y is within the plane. The protrusions 23 and corresponding receptacles 28 are configured to prevent movement of the segments 20 out of the plane. Further, the corresponding tabs 26 and slots 34 are configured to prevent movement of the segments 20 out of the plane, while still allowing movement in the plane. The sidewalls 33 of the tabs 26 contact against the corresponding sidewalls 37 of the slots 34 to prevent the movement out of the plane.

The segments 20 are attached together to expose the cutting surfaces 32 as the device 10 moves through the intervertebral space. In one embodiment, the cutting surfaces 32 are positioned on just one of the ends 21, 22 of the segments 20. Cutting surfaces 32 may also be positioned on both ends 21, 22 to allow cutting when the device 10 is moving in any direction. Further, cutting surfaces 32 may only be positioned on a single lateral side of the segments 20.

The articulating action further causes the cutting surfaces 32 to be exposed different amounts depending upon the angular orientation of the segments 20. This usually means that the cutting surfaces 32 on the outer side of the curvature are exposed. As illustrated in FIG. 5, cutting surfaces 32 positioned on the second sections 31 are exposed as the segments 20 are angled in the first direction X. The cutting surfaces 32 contact against and cut the disc as the device 10 moves into the intervertebral space. Cutting surfaces 32 on the first sections 30 are shielded by the second ends 22 of the adjacent segments 20 and are prevented from cutting the disc.

A distal member 40 may be positioned at the end of the device 10 that is inserted into the intervertebral space. FIG. 1 includes a distal member 40 with a distal end 12 that faces away from the segments 20. The distal end 12 includes a tapered tip that facilitates insertion into the patient. The tip may also be spherical to again facilitate insertion. The distal member 40 also includes a second end 42 that faces towards the segments 20. The second end 42 is configured to attach to one of the segments 20 and includes a pair of receptacles 28 and a slot 34 to receive a corresponding pair of protrusions 23 and tab 26 on the adjacent segment 20. The distal member 40 may include a hollow interior that is bounded by the distal end 41, or may include a solid interior.

Figure 9:
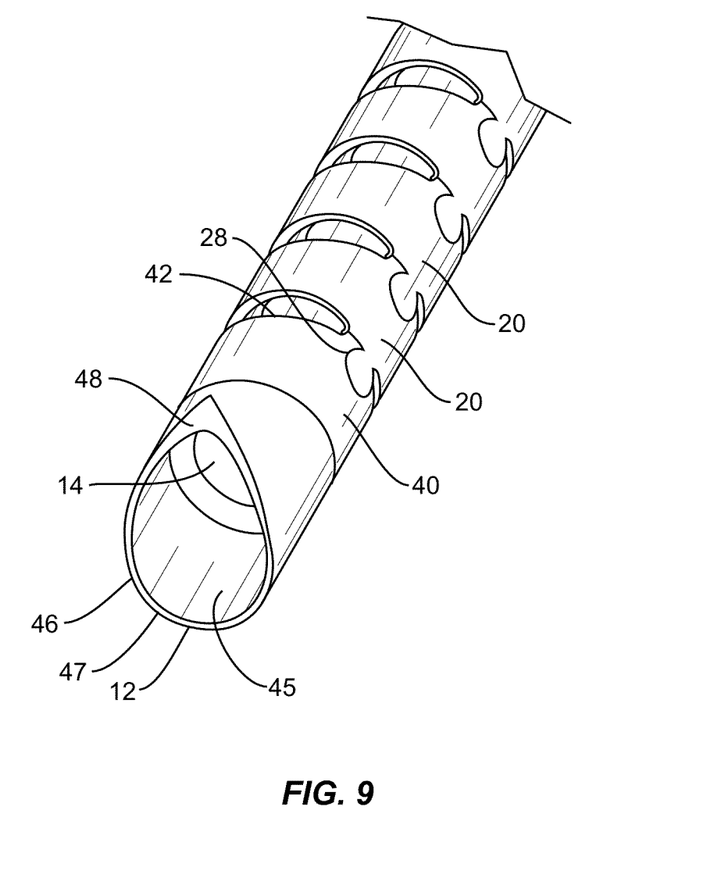
FIG. 9 is a perspective view of a distal member according to one embodiment.

FIG. 9 illustrates another embodiment of a distal member 40. The distal member 40 includes an open end 45 that leads into the interior 14 of the device 10. The open end 45 includes a sharpened edge 46 that is capable of cutting tissue. The end 45 has a slanted orientation with a first side 47 extending axially farther than an opposing second side 48.

The proximal member 50 includes a proximal end 51 and a second end 52. The second end 52 may be configured to attach to the adjacent segment 20. FIG. 1 includes the proximal member 50 including a pair of protrusions 23 and a tab 26. The proximal member 50 may include a hollow interior, or may have a solid interior. The second end 52 may also be configured for attachment to an insertion tool for inserting and manipulating the device 10 within the intervertebral disc space.

Figure 8:
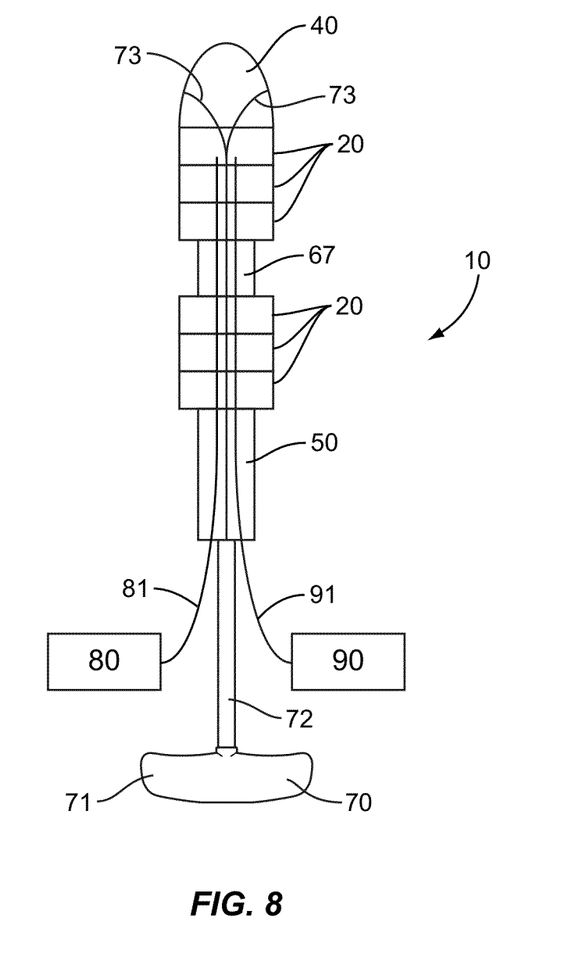
FIG. 8 is a schematic sectional view of a device according to one embodiment.

The device 10 may include a mechanism to adjust the angular position. FIG. 8 illustrates a drive mechanism 70 that includes a handle 70 positioned outward beyond the proximal member 50. One or more elongated adjustment members 73 are connected to the handle 70 and extend through the interior of the device 10. The members 73 are connected to one or more of the segments 20 and the distal member 40 and provide a force to cause articulation of the device in the first and second directions.

The device 10 may also provide irrigation to facilitate the cutting process. As illustrated in FIG. 8, an irrigation system includes a reservoir 80 and one or more conduits 81 that extend into the interior of the device 10. The conduits may be positioned at one or more locations along the length of the device 10. A suction system may also be associated with the device 10 to remove the cut tissue and/or the irrigation fluid. The suction system may include a suction source 90 and one or more conduits 91 leading into the interior of the device 10.

The interior 14 may be hollow along the entire length of the device 10 (i.e., between the distal and proximal ends 12, 13), or may be hollow along one or more limited sections of the length.

The device 10 may include segments 20 along the entirety of the length as illustrated in FIG. 5. One or more non-articulating sections 67 may also be positioned along the device 10 as illustrated in FIG. 8. These sections 67 do not articulate, and may include various shapes and sizes. The sections 67 may be positioned at various locations along the device 10.

The tab 26 may extend outward from the first end 21 of the body 38 and the slot 34 may extend into the second end 22 of the body 38. Other embodiments may include this orientation reversed with the tab 26 on the second end 22 and the slot 34 on the first end 21.

The device 10 may be used within a living patient for the treatment of various spinal disorders. The device 10 may also be used in a non-living situation, such as within a cadaver, model, and the like. The non-living situation may be for one or more of testing, training, and demonstration purposes.

Spatially relative terms such as "under", "below", "lower", "over", "upper", and the like, are used for ease of description to explain the positioning of one element relative to a second element. These terms are intended to encompass different orientations of the device in addition to different orientations than those depicted in the figures. Further, terms such as "first", "second", and the like, are also used to describe various elements, regions, sections, etc and are also not intended to be limiting. Like terms refer to like elements throughout the description.

As used herein, the terms "having", "containing", "including", "comprising" and the like are open ended terms that indicate the presence of stated elements or features, but do not preclude additional elements or features. The articles "a", "an" and "the" are intended to include the plural as well as the singular, unless the context clearly indicates otherwise.

The present invention may be carried out in other specific ways than those herein set forth without departing from the scope and essential characteristics of the invention. The present embodiments are, therefore, to be considered in all respects as illustrative and not restrictive, and all changes coming within the meaning and equivalency range of the appended claims are intended to be embraced therein.

What is claimed is:

1. A device to cut an intervertebral disc comprising:
a plurality of cylindrical segments each having a first end and an opposing second end positioned a fixed distance apart, the first end having a pair of protrusions extending outwardly from a first end surface, the protrusions being positioned on opposing sides of the segment, the first end including a tab extending outwardly from the first end surface and positioned between the protrusions, the first end surface having a continuous convex curvature between the tab and at least one of the protrusions, the second end having a pair of receptacles having a shape that matches the pair of protrusions and being on the same opposing sides of the segment, the second end including a slot configured for disposal of the tab, one of the first and second ends having a sharpened cutting surface;
the plurality of segments attached in an end-to-end articulating arrangement with the protrusions of a first one of the plurality of segments positioned in the receptacles of an adjacent one of the plurality of segments;
the protrusions and the receptacles being attached together and aligned along a longitudinal axis for the plurality of segments to be movable in a variety of angular positions in a first plane and prevented from moving in a second plane that is perpendicular to the first plane,
wherein the cutting surface is defined by at least one of a first portion of the first end surface extending between the tab and one of the protrusions and a second portion of the first end surface extending between the tab and the other protrusion, each of the segments including a non-cutting surface positioned between the pair of protrusions.

2. The device of claim 1, further comprising a distal end member attached to one of the plurality of segments, the distal end member including an open end that leads into an open interior formed by the plurality of segments.

3. The device of claim 1, wherein each of the protrusions includes an enlarged rounded head with a first width and a neck with a smaller second width, and each of the receptacles includes an inlet that extends in from the second end and receives the neck and an enlarged receiving area farther from the second end with a greater width than the neck that receives the head.

4. The device of claim 1, further comprising a distal end member attached to one of the plurality of segments, the distal end member including a tapered tip that faces away from the plurality of segments.

5. The device of claim 1, wherein the second end of at least one of the plurality of segments includes a second cutting surface.

6. The device of claim 1, wherein the tab that has a straight shape and the slot has a shape that matches the tab.

7. A device to cut an intervertebral disc comprising:
an elongated body having a plurality of segments arranged in an end-to-end orientation, each of the segments having:
a pair of protrusions extending outwardly from a first end surface,
a pair of receptacles extending through a second end surface opposite the first end surface,
a tab extending outwardly from the first end surface, the tab being positioned between the protrusions, and
a slot extending through the second end surface,
wherein the first end surface has a continuous convex curvature between the tab and at least one of the protrusions;
a plurality of articulating joints positioned along a length of the body, each of the joints formed by one of the pair of protrusions positioned within one of the pair of receptacles;
a plurality of cutting surfaces positioned along the length of the body; and
a plurality of connections positioned along the length of the body, each of the connections formed by one of the tabs positioned within one of the slots.

8. The device of claim 7, wherein each of the segments includes the pair of protrusions positioned on a first end and opposing sides of the segment, each of the protrusions includes a rounded head and a narrow neck, each of the segments also includes the pair of receptacles positioned on a second end and on the opposing sides of the segment, each of the receptacles includes a narrow inlet and an enlarged receiving area.

9. The device of claim 7, wherein one of the protrusions is positioned on a first side of the device and the other protrusion is positioned on an opposing second side of the device.

10. The device of claim 7, wherein each of the segments includes a fixed shape with a fixed distance between the pair of protrusions and the pair of receptacles.

11. A device to cut an intervertebral disc comprising:
a plurality of segments attached together in an end-to-end orientation and being pivotable relative to each other, each of the plurality of segments including:
a body with a first end and a second end;
a pair of protrusions extending outward from a first end surface of the first end and being spaced apart on opposing sides of the segment;
a pair of receptacles extending into a second end surface of the second end and being spaced apart on the opposing sides of the second end;
a tab extending outwardly from the first end surface, the tab being positioned between the protrusions, the first end surface has a continuous convex curvature between the tab and at least one of the protrusions;
a slot extending through the second end surface;
a first section on the first end positioned at a first angular orientation relative to a longitudinal axis of the segment;

a second section on the first end and spaced apart from the first section and positioned at a different second angular orientation relative to a longitudinal axis of the segment; and a first cutting edge extending along at least one of the first and second sections;

a distal member attached to a distal one of the plurality of segments; and a proximal member attached to a proximal one of the plurality of segments.

12. The device of claim 11, wherein each of the segments includes a cylindrical shape with a hollow interior.

13. The device of claim 11, wherein the distal member includes an open end with a sharpened edge.

14. The device of claim 11, wherein at least one of the plurality of segments includes a second cutting edge extending along the other of the first and second sections.

15. The device of claim 11, further comprising a second cutting edge extending along the second end of at least one of the plurality of segments.

* * * * *